(12) United States Patent
Segman

(10) Patent No.: US 9,996,674 B2
(45) Date of Patent: Jun. 12, 2018

(54) WEB SITE PROVIDING COSMETIC AND NUTRITION REGIMEN FROM COLOR IMAGES

(75) Inventor: Yosef Segman, Zichron Yaacov (IL)

(73) Assignee: CNOGA HOLDINGS LTD., Or Akiva (IL)

(*) Notice: Subject to any disclaimer, the term of this patent is extended or adjusted under 35 U.S.C. 154(b) by 935 days.

(21) Appl. No.: 13/346,765

(22) Filed: Jan. 10, 2012

(65) Prior Publication Data
US 2013/0179298 A1  Jul. 11, 2013

(51) Int. Cl.
*G06F 19/00* (2018.01)
(52) U.S. Cl.
CPC ................ *G06F 19/3456* (2013.01)
(58) Field of Classification Search
None
See application file for complete search history.

(56) References Cited

U.S. PATENT DOCUMENTS

| 2005/0195316 | A1  |  9/2005 | Kollias et al. |
| 2006/0265244 | A1* | 11/2006 | Baumann ................... 705/2 |
| 2009/0299154 | A1* | 12/2009 | Segman ................... 600/301 |
| 2010/0185064 | A1  |  7/2010 | Bandic et al. |

OTHER PUBLICATIONS

Garcia, "Face Detection Using Quantized Skin Color Regions Merging and Wavelet Packet Analysis," IEEE Transactions on Multimedia, vol. 1, p. 264-277, 1999.*

* cited by examiner

*Primary Examiner* — G. Steven Vanni
(74) *Attorney, Agent, or Firm* — Mark M. Friedman

(57) ABSTRACT

A cosmetic regimen and/or a nutrition regimen is outputted almost instantly to a user who transmits a digital color image, preferably video, of the surface tissue, for example at the face of a human to a web site. The regimen is custom tailored to the surface tissue type of the subject. The surface tissue type is based on value ranges of multiple surface tissue bioparameters, such as surface tissue moisture, surface tissue collagen levels, surface tissue pH and surface tissue sun sensitivity. The system may track changes in the surface tissue parameters between one digital color image provided by a user at one time and a further digital color image provided later.

30 Claims, 9 Drawing Sheets

```
┌─────────────────────────────┐
│       METHOD - 100          │
└─────────────────────────────┘
```

```
┌──────────────────────────────────────────────────────┐
│ USING AT LEAST ONE COLOR IMAGE SENSOR TO DETECT      │
│ RED LIGHT, BLUE LIGHT AND GREEN LIGHT REFLECTED      │
│ FROM A DIGITAL COLOR IMAGE, AND TO PRODUCE A         │
│ SERIES OF SPATIAL TEMPORAL ELECTRIC SIGNALS FROM     │
│ THE DETECTED RED, BLUE AND GREEN LIGHTS              │
└──────────────────────────────────────────────────────┘
                                              ⌐ 110
```

```
┌──────────────────────────────────────────────────────┐
│ A COMPUTER PROCESSOR VERIFYING THAT THE DIGITAL      │
│ COLOR IMAGE IS OF LIVE HUMAN TISSUE BY AT LEAST      │
│ TWO OF (I) COMPARING LEVELS OF RED, BLUE AND         │
│ GREEN TO BOUNDARY-REFERENCE LEVELS, (II)             │
│ COMPARING LEVELS OF RED, BLUE AND GREEN TO EACH      │
│ OTHER AND DETERMINING WHICH LEVEL OF AT LEAST        │
│ ONE OF RED, GREEN AND BLUE IS GREATER THAN           │
│ ANOTHER AT LEAST ONE OF RED, GREEN AND BLUE, (III)   │
│ COMPARING TO A REFERENCE RATIO OR TO A REFERENCE     │
│ RATIO RANGE AT LEAST ONE OF A RATIO OF BLUE/RED, A   │
│ RATIO OF BLUE/GREEN AND A RATIO OF GREEN/RED, AND    │
│ (IV) MEASURING OVER TIME INCREASES OR DECREASES IN   │
│ AT LEAST ONE OF A RATIO OF BLUE/RED, A RATIO OF      │
│ BLUE/GREEN, A RATIO OF GREEN/RED, A LEVEL OF RED,    │
│ A LEVEL OF BLUE AND A LEVEL OF GREEN                 │
└──────────────────────────────────────────────────────┘
                                              ⌐ 120
```

```
┌──────────────────────────────────────────────────────┐
│ IF THE DIGITAL COLOR IMAGE IS DETERMINED TO BE       │
│ HUMAN TISSUE, A COMPUTER PROCESSOR GENERATING A      │
│ COLOR INTENSITY DISTRIBUTION OVER TIME FROM THE      │
│ SERIES OF ELECTRIC SIGNALS OVER TIME                 │
└──────────────────────────────────────────────────────┘
                                              ⌐ 130
```

FIG. 4A

METHOD – 100 (CONTINUED)

THE COMPUTER PROCESSOR, FOR EACH OF AT LEAST TWO SURFACE TISSUE PARAMETERS RELATING TO A SURFACE TISSUE OF THE HUMAN AND INCLUDING AT LEAST ONE OF SURFACE TISSUE PH, SURFACE TISSUE MOISTURE, SURFACE TISSUE COLLAGEN LEVEL AND SURFACE TISSUE SUN SENSITIVITY, PRODUCING A MEASUREMENT VALUE OF THE EACH SURFACE TISSUE PARAMETER OF THE AT LEAST TWO SURFACE TISSUE PARAMETERS BY ANALYZING THE COLOR INTENSITY DISTRIBUTION OF THE FIRST, SECOND AND THIRD COLOR IN SPACE OVER TIME AND IDENTIFYING AT LEAST ONE OF A CORRELATION AND A LOOK-UP TABLE BETWEEN A LEVEL OF THE EACH SURFACE TISSUE PARAMETER AND AT LEAST ONE OF COLOR DISTRIBUTION AND ANY CHANGES IN COLOR DISTRIBUTION IN A COLOR INTENSITY DISTRIBUTION OVER TIME OF ANY OF THE FIRST COLOR, THE SECOND COLOR, AND THE THIRD COLOR

— 140

THE PROCESSOR CONVERTING EACH MEASURMENT VALUE INTO A VALUE RANGE, EACH SURFACE TISSUE PARAMETER HAVING AT LEAST THREE VALUE RANGES

— 150

USING EACH VALUE RANGE OR VALUE OF EACH OF THE AT LEAST TWO/THREE SURFACE TISSUE PARAMETERS, A COMPUTER PROCESSOR IDENTIFYING A SURFACE TISSUE TYPE ASSOCIATED WITH THE DIGITAL IMAGE FROM A MULTIPLICITY OF SURFACE TISSUE TYPES

METHOD – 100 (CONTINUED)

A COSMETIC TREATMENT OUTPUT MODULE OUTPUTTING TO THE USER A COSMETIC REGIMEN BY MATCHING AN IDENTIFIED SURFACE TISSUE TYPE WITH ONE OR MORE COSMETIC PRODUCTS, SUCH THAT EACH COSMETIC PRODUCT OF THE ONE OR MORE COSMETIC PRODUCTS IMPROVES AT LEAST ONE SURFACE TISSUE PARAMETER OF THE HUMAN SUBJECT WITHOUT WORSENING ANY OTHER SURFACE TISSUE PARAMETER OF THE AT LEAST TWO SURFACE TISSUE PARAMETERS OF THE HUMAN SUBJECT

WEB SITE PROVIDING COSMETIC AND NUTRITION REGIMEN FROM COLOR IMAGES

FIELD AND BACKGROUND OF THE INVENTION

The present invention relates to apparatuses and methods for cosmetic and nutrition regimens, and, more particularly to outputting a cosmetic and/or nutrition regimen from a digital color image of a face or other surface tissue of a person that was transmitted to a web site.

Cosmetic products for the skin and hair need to be custom tailored to the skin or hair of the individual user. It is known to have different soaps for example that are for oily surface tissue or for dry skin. However, not all cosmetic products can, as a practical matter, take into consideration the exact skin type or hair type of each consumer. Consumers may not have the time or patience to go to a cosmetic counter in certain stores and have their skin type checked. In addition, it is not commonly known how to determine skin type within a time frame that can be useful for consumers of cosmetic products. Furthermore, there are many variables that affect one's skin type and there are many different cosmetic products. In addition, the skin type of a cosmetic consumer may change and the information may not be current at the time of purchase.

It would also be useful to have a nutrition regimen for improved health and lifestyle and disease prevention that makes use of current bioparameters of the individual. Most people do not have the benefit of nutrition consultants unless they are under treatment and require a medically supervised diet. Furthermore, nutrition consultants may be advised of the physiological history of the subject but may not have the most current information of each bioparameter.

There is a compelling need to have an apparatus and method that will provide almost instant cosmetic and/or nutrition regimens to individuals that are custom tailored to that individual's bioparameters.

SUMMARY OF THE PRESENT INVENTION

One aspect of the present invention is a system for providing a cosmetic regimen, comprising a computer server associated with a web site, at least one of the computer server and the web site configured to prompt a user to digitally transmit a digital color image of a surface tissue of a human subject to the computer server; a computer memory for storing (i) the digital color image, (ii) a multiplicity of surface tissue types, (iii) at least one of a list of cosmetic products and a list of nutrition products, and (iv) a table matching each surface tissue type to a product from the list, at least one color digital image sensor configured to detect a spectrum of colored light of a first color, a spectrum of color light of a second color and a spectrum of colored light of a third color, and to produce a series of electric signals over time; a processing unit configured to generate a color intensity distribution over time from the series of electric signals over time and, for each of at least two surface tissue parameters relating to the surface tissue of the human, configured to produce a measurement value of the each surface tissue parameter of the at least two surface tissue parameters by analyzing the color intensity distribution of the first, second and third color in three dimensional space over time and identifying at least one of a correlation and a look-up table between a level of the each surface tissue parameter and at least one of (i) color distribution and (ii) changes, if any, in color distribution in a color intensity distribution over time of any of the first color, the second color, and the third color, the processor configured to convert each measurement value into a value range, each surface tissue parameter having at least three value ranges; a computer processor configured, using each value range of each of the at least two surface tissue parameters, to identify a surface tissue type associated with the digital image from the multiplicity of surface tissue types; and a cosmetic treatment output module for outputting to the user a cosmetic regimen by using the table to match an identified surface tissue type with one or more cosmetic products such that each cosmetic product of the one or more cosmetic products improves at least one surface tissue surface tissue parameter of the human subject without worsening any other surface tissue parameter of the at least two surface tissue parameters of the human subject, each surface tissue type representing a collection of value ranges for different particular surface tissue parameters of the at least two surface tissue parameters, the number of surface tissue types equaling $X^Y$, wherein X is a number of value ranges and Y is a number of different surface tissue parameters, wherein X is at least three and wherein Y is at least 2.

A further aspect of the present invention is directed to a method of providing a cosmetic and nutrition regimen for a human from digital color video image of a surface tissue of the human sent to a web site, comprising using at least one color image sensor to detect red light, blue light and green light reflected from a digital color image, and to produce a series of spatial temporal electric signals from the detected red, blue and green lights; a computer processor verifying that the digital color image is of live human tissue by at least two of (i) comparing levels of red, blue and green to boundary-reference levels, (ii) comparing levels of red, blue and green to each other and determining which level of at least one of red, green and blue is greater than another at least one of red, green and blue, (iii) comparing to a reference ratio or to a reference ratio range at least one of a ratio of blue/red, a ratio of blue/green and a ratio of green/red, and (iv) measuring over time increases or decreases in at least one of a ratio of blue/red, a ratio of blue/green, a ratio of green/red, a level of red, a level of blue and a level of green; if the digital color image is determined to be live human tissue, a computer processor generating a color intensity distribution over time from the series of spatial temporal electric signals; the computer processor, for each of at least two surface tissue parameters relating to the surface tissue of the human and including at least one of surface tissue pH, surface tissue moisture, surface tissue collagen level and surface tissue sun sensitivity, producing a measurement value of the each surface tissue parameter of the at least two surface tissue parameters by analyzing the color intensity distribution of the first, second and third color in space over time and identifying at least one of a correlation and a look-up table between a level of the each surface tissue parameter and at least one of color distribution and any changes in color distribution in a color intensity distribution over time of any of the first color, the second color, and the third color; the processor converting each measurement value into a value range, each surface tissue parameter having at least three value ranges; using each value range or value of each of the at least two surface tissue parameters, a computer processor identifying a surface tissue type associated with the digital image from a multiplicity of surface tissue types; and a cosmetic treatment output module outputting to the user a cosmetic regimen by matching an identified surface tissue type with one or more cosmetic products, such that each cosmetic product of the one or more cosmetic products improves at least one surface tissue parameter of the human subject without worsening any other surface tissue parameter of the at least two surface tissue parameters of the human subject.

A still further aspect of the present invention is a non-transitory computer-readable medium having embedded thereon computer-readable code for storing in a computer memory device, the computer-readable code comprising program code for verifying whether a series of spatial temporal electric signals corresponding to a digital color image of a surface tissue is an image of live human tissue; program code for generating a color intensity distribution of three colors of the digital color image over time, if the series of electric signals does correspond to the digital color image of human tissue; program code for analyzing the color intensity distribution of the series of electric signals using at least one of a correlation and a look-up table; program code for producing measurement values of at least two surface tissue bioparameters of the subject of the digital color image; program code for converting the measurement values to value ranges, each surface tissue parameter having at least three value ranges; program code for identifying a surface tissue type associated with the digital image amongst a multiplicity of surface tissue types using each value range of each of the at least two surface tissue parameters.

A yet still further aspect of the present invention is directed to a system comprising a computer memory device for storing (i) a digital color image sent by a user, (ii) a multiplicity of surface tissue types, (iii) at least one of a list of cosmetic products and a list of nutrition products, and (iv) a table matching each surface tissue type to at least one of a cosmetic product and a nutrition product, a host of the computer memory device, the host including a processor for executing computer-readable program code embedded in a non-transitory computer-readabloe medium, the computer-readable code comprising program code for verifying whether a series of spatial temporal electric signals corresponding to a digital color image of a face is an image of live human tissue; program code for generating a color intensity distribution of three colors of the digital color image over time, if the series of electric signals does correspond to the digital color image of human tissue; program code for analyzing the color intensity distribution of the series of electric signals using at least one of a correlation and a look-up table; program code for producing measurement values of at least two surface tissue bioparameters of the subject of the digital color image; program code for converting the measurement values to value ranges, each surface tissue parameter having at least three value ranges; program code for identifying a surface tissue type associated with the digital image amongst a multiplicity of surface tissue types using each value range of each of the at least two 1.0 surface tissue parameters.

These and other features, aspects and advantages of the present invention will become better understood with reference to the following drawings, descriptions and claims.

BRIEF DESCRIPTION OF THE DRAWINGS

Various embodiments are herein described, by way of example only, with reference to the accompanying drawings, wherein:

FIGS. 4A-4C show a flow chart of a method, in accordance with one embodiment of the present invention;

DETAILED DESCRIPTION OF THE INVENTION

Figure 1:
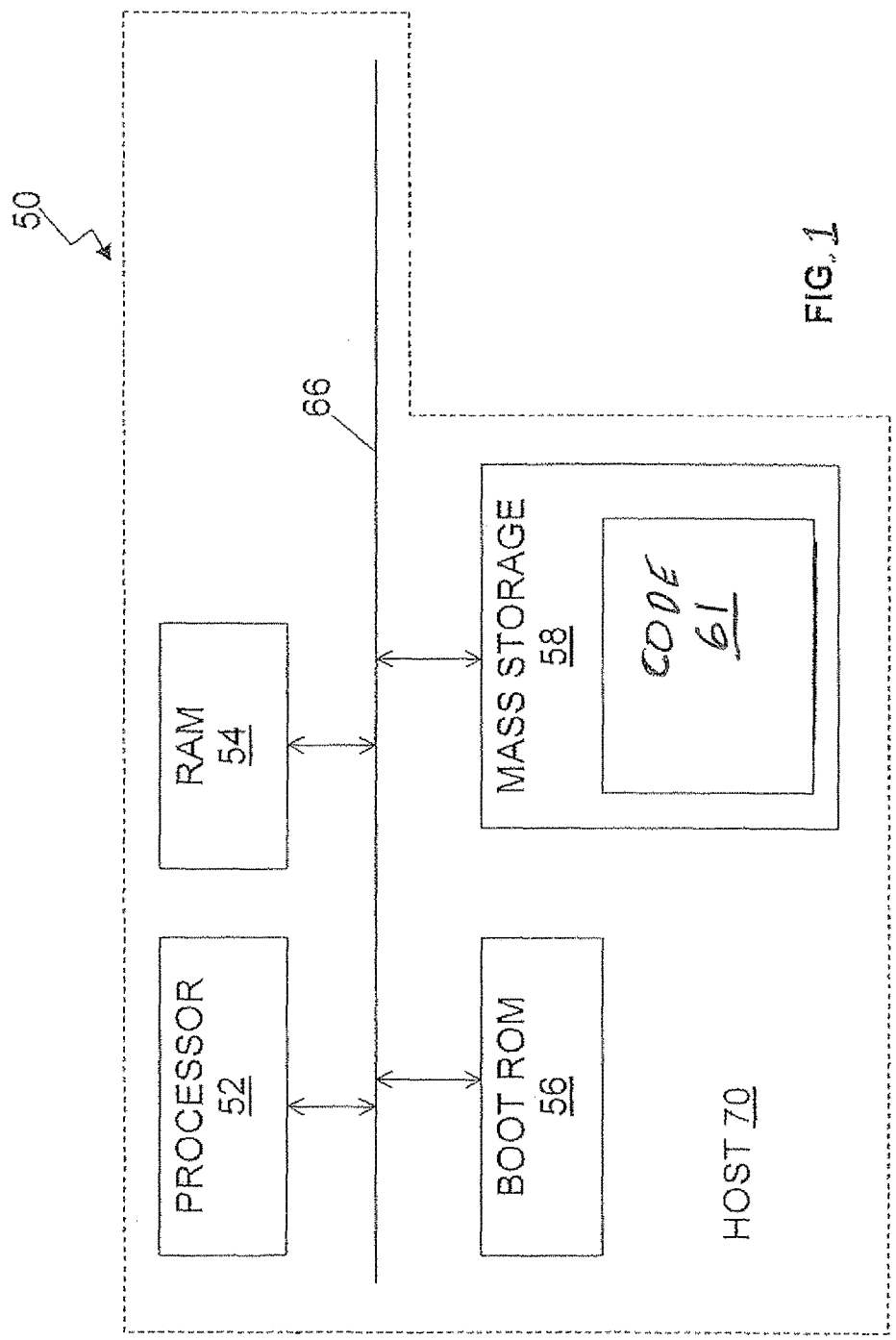
FIG. 1 is a high-level schematic block diagram of a computer system, in accordance with one embodiment of the present invention.

The following detailed description is of the best currently contemplated modes of carrying out the invention. The description is not to be taken in a limiting sense, but is made merely for the purpose of illustrating the general principles of the invention, since the scope of the invention is best defined by the appended claims.

The present invention generally provides a web site that may receive and may prompt users to send a digital video color image of a human face from a light source such as daylight, ambient light or an ultra violet light source. At least one color image sensor detects the red, blue and green light at each spatial coordinates of the digital color image over time. The computer processor may verify that the image is of live human tissue and if it is, generates a color intensity distribution of the image. A computer processor processes the image. For each of at least two surface tissue parameters relating the face of the human subject, including at least two amongst surface tissue pH, surface tissue moisture, surface tissue collagen level and surface tissue sun sensitivity, the compute processor produces a measurement value by analyzing the color intensity distribution of the three colors over time and finds a correlation and/or a look up table between the level of each parameter and changes in color distribution or the color distribution and converts the measurement values into value ranges, each surface tissue parameter having at least three value ranges. A surface tissue type is identified and matched with cosmetic and/or nutrition products to produce a cosmetic and/or nutrition regimen within a few seconds in most cases.

In contrast to prior art cosmetic regimens which require touching the subject's surface tissue or require being in the presence of the subject to generate the regimen, the method and apparatus of the present invention only requires a user to transmit a digital image of the subject to a web site. In further contrast to the prior art, in which the regimen is customized for a single surface tissue parameter or one 2 or 3 surface tissue types, the present invention categorizes the subject's surface tissue into one of at least nine surface tissue types and preferably dozens of surface tissue types that take into account between two and eight or more different surface tissue parameters. In contrast to the prior art, the present invention provides both a nutrition and cosmetic regimen from digital images of the face based on surface tissue type. In contrast to the prior art, the present invention verifies that the image is of live human tissue by processing colors of the facial image. In still further contrast to the prior art, in which a cosmetic product may be used to improve a particular surface tissue condition regarding a level of a particular surface tissue parameter, the present invention may provide digitally a cosmetic regimen in which each cosmetic product, or in some preferred embodiments each ingredient of each cosmetic product, improves at least one surface tissue bioparameter without harming any other surface tissue bioparameter. In contrast to prior art cosmetic and/or nutrition regimens, which may use the image of a face visible to the naked eye, the present invention may use a light source such as UV in some preferred embodiments to detect colors invisible to the naked eye.

The principles and operation of a method and apparatus for a web site providing a cosmetic and nutrition regimen from a color digital image may be better understood with reference to the drawings and the accompanying description.

The term "surface tissue" is a phrase intended to encompass both, skin and hair of a subject and is not limited to the skin or hair located only on the face of the subject. "Surface tissue type" includes skin type and hair type. The term "cosmetic regimen" shall be understood to be broad enough to also include regimens for hair. Similarly, the term "cosmetic treatment output module" shall be understood to be broad enough to also include output modules that output regimens for hair. Similarly, "cosmetic products" includes "hair products". "Nutrition product" includes food products as well as other products consumed by users for nutritional purposes. "Nutrition product" does not include educational materials not consumed by the user.

Figure 3:
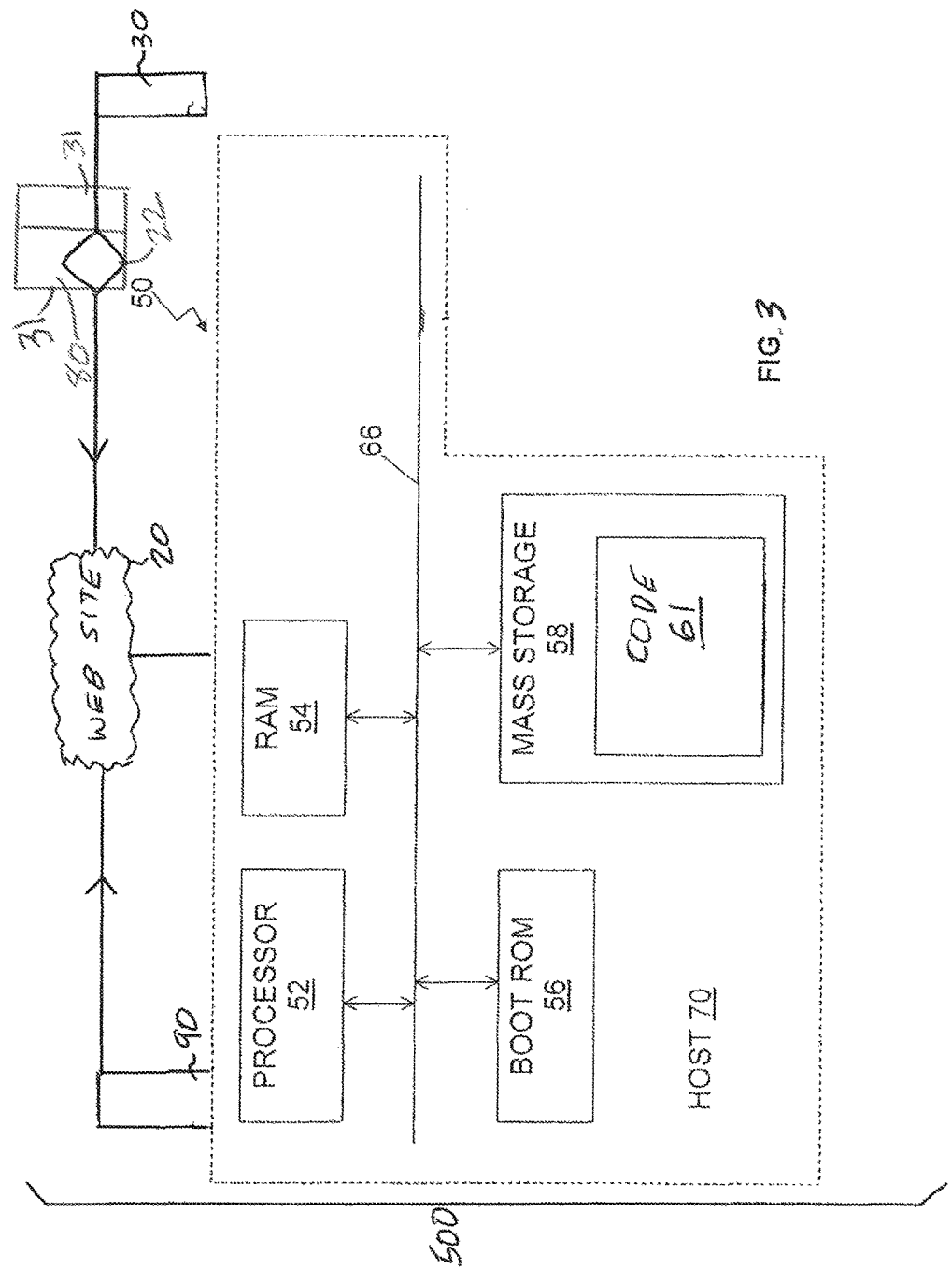
FIG. 3 is a block diagram of a system, in accordance with one embodiment of the present invention.
Figure 5:
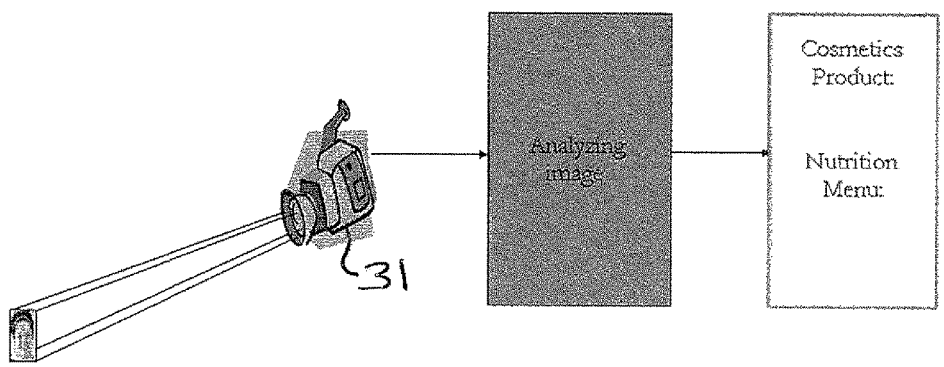
FIG. 5 shows a schematic diagram of a digital color camera capturing a digital image the image being analyzed and the system outputting a cosmetic product and/or a nutrition menu, in accordance with one embodiment of the present invention.

Generally, as seen from FIG. 3, a system 500 of the present invention may provide a cosmetic and/or nutrition regimen from a color digital image (for example a color video image) of a face of a human or of any other surface tissue of a subject transmitted to a web site 20 such as to a computer server 50 associated with a web site 20 via a camera 31 or other user device 31 (FIG. 5). The user device may be a cellular telephone, PAD (iPAD), laptop computer, personal computer, video camera, digital camera and electronic device that may either have color image sensor that can take photo or sequence of photos or real-time sequence of photos such as video stream or any device that has electronic storage (hard drive, flash memory, etc.). The user may enjoy fast response by letting the system use the user device's own computational power to execute part of the software computation on the user device. This reduces traffic over the internet or wi-fi communication.

Figure 6:
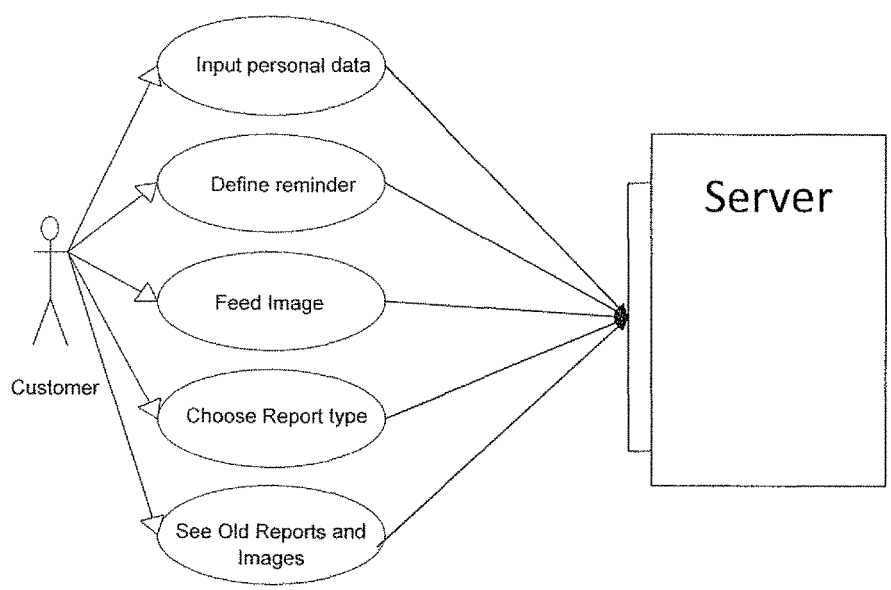
FIG. 6 shows a schematic diagram of a customer in bilateral communications with a server computer including options/prompts by the server to be selected by the customer, in accordance with one embodiment of the present invention.
Figure 7:
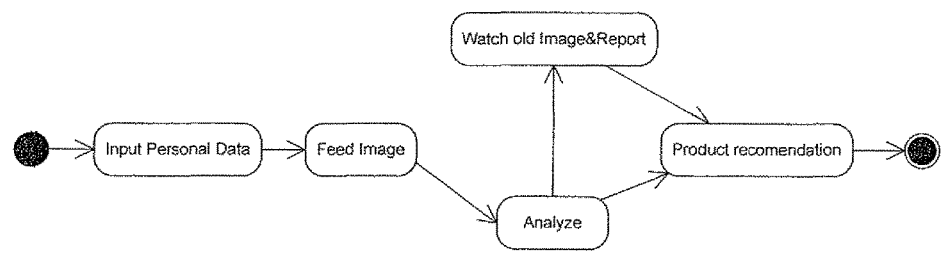
FIG. 7 shows a schematic diagram of a workflow showing steps in accordance with one embodiment of a method of the present invention.
Figure 8:
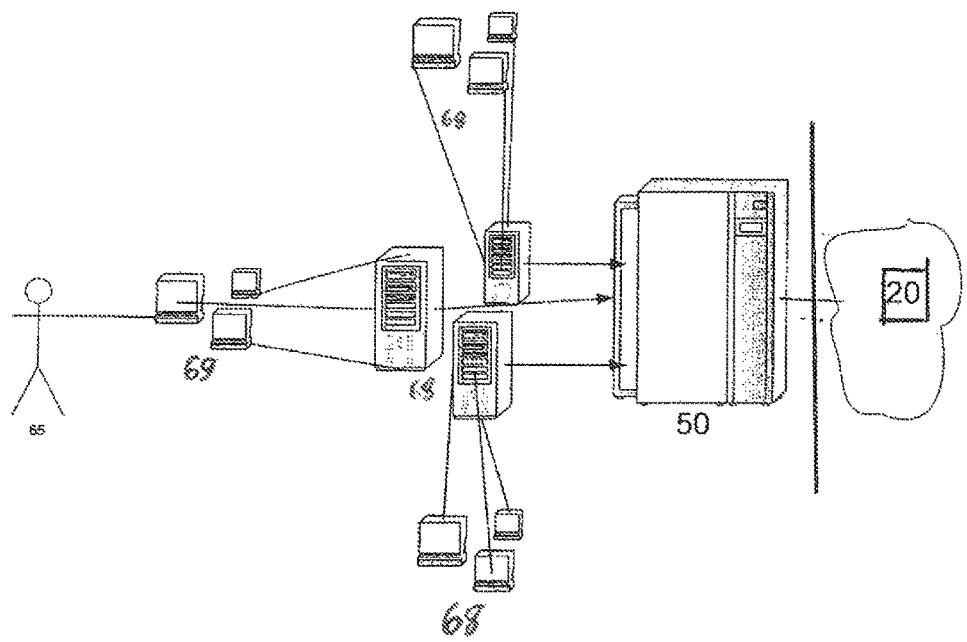
FIG. 8 shows a high level diagram of communication flow between a user/customer and workstations, local computer servers and a central server computer and a web site.

As seen from FIG. 6, the user may communicate with the server 50 and the server 50 may communicate to the user ("customer" in FIG. 6). The server may prompt the user/customer with various options including inputting personal data (including for example name, password, email address, etc.). Once the user/customer is registered with the system, the user may elect to define reminders, input a new digital color image to the server, ask the server computer for an analysis of a digital color image presently or previously inputted, choose the type of report that the user desires to have outputted and review history associated with a human subject, which may be the user. The history may allow reviewing a collection of previously inputted digital color images of the subject of the digital image (which may be the user) which may include reviewing by a pre-selected time period or skin condition or other category such as a particular surface tissue parameter level, reviewing old reports that were previously outputted to the user by the system or server and which may be stored in the user's account, for example at the web site. Furthermore, by reviewing the history, the user may be able to review the progress of a skin condition or a hair condition or a nutrition condition or even a medical condition such as acne, of a subject (which subject may be the user). The system, via the server, may provide quantitative changes in any one or more of the surface tissue parameters and may at the request of the user display graphical depictions and/or reports of the changes in these surface tissue parameters. FIG. 7 depicts a sequence of workflow steps in which the user chose to input personal data and then feed an image for analysis. FIG. 8 shows a system comprising a web site 20 in the World Wide Web 21 or Internet 21, a central server computer 50 that may in communication with and may collect information from local server computers 68. Local servers 68 and that are in communication with workstations 69 that the customer/user 65 may access. Each workstation 69 accessible to the user may include a high quality video camera, a web cam for example, a touch screen, speakers and a local network connection. Each local server 68 may include a local database connection and a number of client machines.

A user may use a light source 30 to capture an image of a face of a human subject. In some preferred embodiments, users have purchased UV light sources from the manager of the system or method of the present invention in order to capture the digital image 22. Otherwise, the digital image 22 of the face may be taken under normal light conditions which means daylight or white ambient light as close to daylight as possible in order to be useful for the surface tissue analysis. Fluorescent light may in some cases be sufficient. A system of the present invention may include a web camera (web cam) that allows the web site 20 itself to be used in the creation of the digital color image of the subject and transmission to the processor in real time.

At least one of the computer server and the web site may be configured to prompt one or more users (including multiple users who may be using different platforms as user devices such laptop, cell phone etc.) and may prompt the user to digitally transmit a digital color image 22 of a tissue surface, such as a face, of a human subject (for example the user) to the computer server. A computer memory may store (i) the digital color image, (ii) a multiplicity of surface tissue types (skin types and/or hair types), (iii) a list of cosmetic products (without hair products) or a list of nutrition products or a list of hair products or a list of all products or other combinations, and (iv) a table matching each surface tissue type to a product, for example a cosmetic product, from the list. The computer memory may also be configured to store a list of foods and a table matching each surface tissue type to a food in the list of foods.

As seen by the high-level block diagram of FIG. 1, a system 50 of the present invention may include a computer processor 52 and may have multiple computer memory devices such as a RAM 54, a boot ROM, a mass storage device 58 such as a hard disk 58. The memory devices may communicate to the processor 52 through a bus 66 and may communicate to each other through a common bus 66. Computer-readable program code 61 may be stored in a memory device such as mass storage device 58 and may be executed by processor 52 to access the memory device. Mass storage device 58 is an example of a non-transitory computer readable storage medium having computer-readable code for implementing the data storage methodology described.

Figure 2:
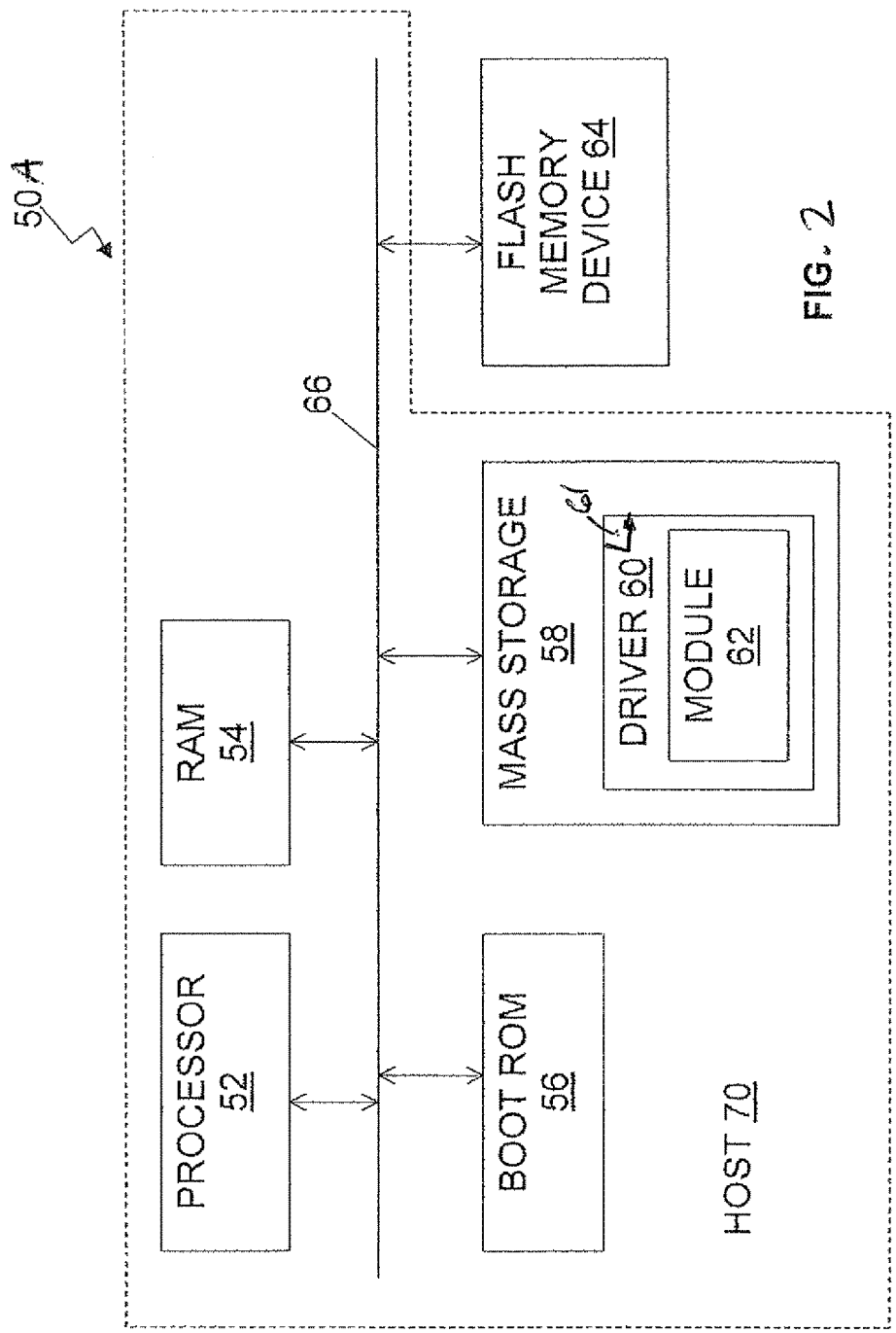
FIG. 2 is a high-level schematic block diagram of a computer system that manages a flash memory device, in accordance with one embodiment of the present invention.

As seen by the high-level block diagram of FIG. 2, a system 50A of the present invention, system 50 may include a computer processor 52 and multiple computer memory devices such as a RAM 54, a boot ROM, a hard disk 58 for mass storage and a flash memory device 64 known in the art. The memory devices may communicate to the processor 52 through a bus 66 and may communicate to each other through a common bus 66. A software driver 60 of a memory device such as flash memory device 64 may be stored in mass storage device 58 and may be executed by processor 52 to access the memory device such as flash memory device 64. Driver 60 may include a module 62 for encoding data to be stored in the memory device such as flash memory device 64 and for decoding codewords received from the memory device such as lash memory device 64. The components of the system 50 other than the flash memory device 64 may comprise a host 70 of flash memory device 64. Mass storage device 58 is an example of a non-transitory computer readable storage medium having computer-readable code 61 for implementing the data storage methodology described.

The computer-readable program code 61 of FIG. 1 (or of FIG. 2) may be embedded in a non-transitory computer readable medium and may be executed by processor 52. The program code 61 may comprise program code for verifying whether a series of spatial temporal electric signals corresponding to a digital color image of a face is an image of live human tissue; program code for generating a color intensity distribution of three colors of the digital color image over time, if the series of electric signals does correspond to the digital color image of human tissue; program code for analyzing the color intensity distribution of the series of electric signals using at least one of a correlation and a look-up table; program code for producing measurement values of at least two surface tissue bioparameters of the subject of the digital color image; program code for converting the measurement values to value ranges, each surface tissue parameter having at least three value ranges; program code for identifying a surface tissue type associated with the digital image amongst a multiplicity of surface tissue types using each value range of each of the at least two surface tissue parameters and at least one of (i) program code for matching the surface tissue type with cosmetic products to produce a cosmetic regimen and (ii) program code for matching the surface tissue type with food prducts to produce a nutrition regimen. In certain cases, program code for performing one or more of these functions may be installed on the user device to reduce digital traffic between the user device and the server of the system of the present invention and thereby accelerate responsiveness of the method and apparatus of the present invention.

As seen from FIG. 3, a system 500 of the present invention may include the computer components of FIG. 1 as well as other components including a color image sensor 80. The color of the surface tissue may be ascertained at different depths of the surface tissue, for example the epidermis and the deeper surface tissue layers.

At least one color image sensor 80 (which may include one color video image sensor for each color and which may be a color video image), which may be of a user device or which may be a user device, may be configured to detect a spectrum of colored light of a first color, a spectrum of colored light of a second color and a spectrum of colored light of a third color and to produce a series of spatial temporal electric signals over time. The user device may then send a digital color image to the server 50 which may be associated with or located at web site 20. The term "electric signals over time" shall be understood to refer to spatial temporal electric signals. A series of color images 22 in video (having one or more different digital images of the face of the subject) of the face or other surface tissue of a human subject may be taken by the user and transmitted to the web site computer server. At least one color image sensor 80 may include a first photodetector that may be configured to detect a spectrum of colored light of a first color such as red from this series of color images (i.e. video) in spatial temporal color space. The first photodetector may then produce a first series of spatial temporal electric signals associated with the colored light of the first color and send the electric signals to a processing unit, A second photodetector (or the first photodetector) may be configured to detect a spectrum of colored light of a second color such as blue from this series of color images (i.e. video) in spatial temporal color space and likewise produce a second series of spatial temporal electric signals associated with the colored light of the second color and send the electric signals to the processing unit. A third photodetector (or the first or second photodetector) may be configured to detect a spectrum of colored light of a third color such as green from the series of color images (i.e. video) in spatial temporal color space. The third photodetector (which may be the first or second photodetector) may then produce a third series of spatial temporal electric signals associated with the colored light of the third color and send the electric signals to a processing unit. If digital color image 22 is a color video image, it contains at least two different images over time.

A computer processor (which may be processor 52) may first verify that the digital color image 22 is of live human tissue by utilizing at least two and preferably all of the following calculations known in the art: (i) comparing levels of red, blue and green to boundary-reference levels since each of the three colors has upper and lower boundaries known in the art to be realistically possible to be live human subjects, (ii) comparing levels of red, blue and green to each other and determining which level of at least one of red, green and blue is greater than another at least one of red, green and blue (and preferably comparing red to blue, red to green and blue to green) since a live human subject has a level of red color greater than green, a level of red greater than blue and a level of green that is usually greater than blue, (iii) comparing to a reference ratio or to a reference ratio range at least one of a ratio of blue/red, a ratio of blue/green and a ratio of green/red, and (iv) measuring over time increases or decreases in at least one of a ratio of blue/red, a ratio of blue/green, a ratio of green/red, a level of red, a level of blue and a level of green. For a live human, measured over time, there should be increases and decreases in color levels. If the levels are flat over time, this means that the image is of a dead person or of an inanimate object or that there was something wrong with the light source. If the digital color image is determined to be or not likely to be that of live human tissue, the output module 90 may output a message "tissue not recognized" and advise the user to try changing the light being used to generate the digital color image to make sure to utilize daylight or white ambient light as close to daylight as possible.

If the digital color image/video is determined to be live human tissue, a computer processor may generate a color intensity distribution over time from the series of spatial temporal electric signals. This may include a color distribution of each color over time.

For example the at least one color image sensor make take one-hundred twenty frames of the face over a two second interval. The computer processor (which may be processor 52) may then create a vector (an ordered collection) or may create an unordered collection of the one-hundred twenty values for each the three colors (i.e. red, green, blue). For example, each of the one-hundred twenty values for red, may represent an average of the level of red over all the pixels (coordinates or locations) within the image at that temporal coordinate at point within the two second interval. The processor may analyze the vector using correlations and/or look-up tables for surface tissue bioparameters.

The computer processor, for each of at least two surface tissue parameters (and preferably at least three surface tissue parameters) relating to a surface tissue of the face and including at least one of surface tissue pH, surface tissue moisture, surface tissue collagen level and surface tissue sun sensitivity, may produce a measurement value of the each surface tissue parameter by analyzing the color intensity distribution of the first, second and third color in space (for example three dimensional space) over time and identifying at least one of a correlation and a look-up table between a level of the each surface tissue parameter and at least one of color distribution and any changes in color distribution in a color intensity distribution over time of any of the first color, the second color, and the third color. In some preferred embodiments, the surface tissue parameters measured include surface tissue moisture levels, surface tissue collagen levels, surface tissue sun sensitivity and surface tissue pH. In other preferred embodiments, they include at least three or at least two of these four.

For each surface tissue bioparameter under consideration there may be a color map e.g. look up table that may correlate between the color and bioparameter. The color map may be a function of the following independent parameters: time (temporal parameter), location within the image (i.e. pixel) (spatial parameter) and at least three basic colors such as red, green, blue. The color map may also be a function of certain additional dependent parameters including temporary histograms of each color, ratios of groups of two colors such as blue/red, blue/green, green/red and certain normalization factors such Euclidian norm.

In some preferred embodiments, in case additional information beyond that provided from the digital color image 22 itself is available, such information may be used to better determine the physiological status of the individual. For example, the additional information may include surface tissue temperature, surface tissue smell, tissue conductivity, surface tissue saltiness etc. or other parameters that may be useful for the surface tissue parameter of the human subject. The additional information may be sent, for example by the user, to the web server for use in a thorough analysis of the surface tissue of the human subject. Based on this analysis, cosmetic and/or nutrition, or even medical, recommendation may be suggested.

A user may communicate a request, for example to the server that the cosmetic or nutrition regimen be tailored to a specific condition, such as acne. In that case, the system may process such a request and select the regimen based in part on the fact that the user has such a condition.

Users may provide feedback to the computer server in two ways. First, users have repeat their request for an output of cosmetic or nutrition regimen and in so doing may send an updated digital color image to the server. This may occur a number of times such as 3, 5, 10 or more times if the user uses the method or apparatus of the present invention over and over. Accordingly, the present invention may include a tracking feature that tracks changes in the surface tissue parameter(s) of the human subject and reports the improvement or decline in one or more surface tissue parameters to the user. For example, the second digital color image (video) may show a 2% change improvement in skin pH or in skin collagen or in skin redness or in skin moisture, etc. The user may be notified, for example, at the user's own system account when the user logs in to the web site for example. An email notification may be sent to the user.

A second source of user feedback is a communication from the user reporting that the human subject has experienced an improvement (or a decline) regarding a surface tissue parameter. For example, the user may report that after using the cosmetic products recommended by the cosmetic treatment output module, her skin (in the case the user is the subject) has become more moist, more red, etc. Whether the user's statement is objectively true may be evaluated by the processor using the method and apparatus of the present invention.

The computer processor may be configured to convert and may convert each measurement value into a value range, with each surface tissue parameter having at least three value ranges. An example of a set of three value ranges include low, normal and high. An example of a set of five value ranges would be very low, low, normal high and very high. Typically, there may be one single computer processor that performs all the functions mentioned that a computer processor performs. In other preferred embodiments, multiple computer processors perform such functions.

The computer processor may be configured to identify, using each value range of each of at least two and preferably at least three surface tissue parameters and may identify a surface tissue type associated with the digital color image (for example a digital video color image) from the multiplicity of surface tissue types. Each surface tissue type represents a collection of value ranges for different particular surface tissue parameters of the at least two three surface tissue parameters, the number of surface tissue types may equal $X^Y$, wherein X is a number of value ranges and Y is a number of different surface tissue parameters, wherein X is at least three and wherein Y is at least 2. The minimum breadth of the value range is a single value point.

A particular illustrative surface tissue type may describe a subject who has a very low level of surface tissue moisture, a normal level of surface tissue collagen, a high level of surface tissue sun sensitivity and a normal level of surface tissue pH. In this case there were five value ranges (very low, low, normal, high very high) and four surface tissue parameters also called surface tissue bioparameters (surface tissue moisture, surface tissue collagen, surface tissue sun sensitivity, and surface tissue pH) yielding $5^4$ or 625 possible surface tissue types.

The particular surface tissue parameters for which value ranges may be measured to generate this collection or vector may include (i) the amount of surface tissue moisture, where 35% may be considered normal, (ii) amount of collagen in the surface tissue which may be represented as a concentration where 75% may be considered normal, (iii) the pH of the surface tissue, where 5.5 may be considered normal and (iv) the sensitivity of the surface tissue to the sun ("sun sensitivity"), where 50% may be considered normal. The surface tissue parameters may also include oxygen concentration where greater than 90% may be considered normal, carbon dioxide concentration where 25%-30% may be considered normal, surface tissue pigmentation where 25% to 40% may be considered normal, surface tissue saturation where greater than 75% may be considered normal, surface tissue redness where less than 40% may be considered normal and surface tissue vitality, where over 80% may be considered normal. Other surface tissue bioparameters may also be used.

Computation of the surface tissue bioparameters may draw on the general idea that the color image 22 of human tissue, such as surface tissue, may provide information about the subject's physiological status. The processing unit 52 may be configured to receive and electronically process the first, second and third series of electric signals to generate output comprising a color distribution in spatial temporal color space including a change in color distribution of the first color (i.e. red) in spatial temporal color space, a change in color distribution of the second color (i.e. blue) in spatial temporal color space and a change in color distribution of the third color (i.e. green) in spatial temporal color space in the facial tissue of the subject.

The processing unit may further process the output and identify a correlation and/or a look-up table between a level or a value range of particular surface tissue bioparameters and changes in color distribution in spatial temporal color space of any of the first color, the second color, and the third color to produce a measurement of the surface tissue bioparameter.

Spo2, CO2, O2, pH, SpCo2 may be measured by analyzing the color distribution between red, green and blue.

Arterial blood is pinker than venal blood which is bluer. Arterial blood (with certain exceptions such as the pulmonary artery) carries oxygenated hemoglobin and is redder whereas venal blood carries deoxygenated hemoglobin and carbon dioxide and is bluer. When the tissue color captured by the photodetectors (either surface tissue or blood tissue beneath the surface tissue) tends toward pink (i.e. the ratio of red to blue increases over time) that may indicate that the level of oxygen (and of $PO_2$ and $SPO_2$) of the subject may be increasing because oxygenated blood is redder than deoxygenated blood. Conversely if the color of the tissue (either surface tissue or blood tissue beneath the surface tissue) captured by the photodetectors tends toward blue (i.e. the ratio of red to blue decreases over time) or blue-purple that may indicate that the level of oxygen (and of $PO_2$ and $SpO_2$) of the subject may be decreasing and the level of carbon dioxide (and of $PCO_2$ and $SpCO_2$) may be increasing. The pH of the captured tissue may be more acidic if the level of carbon dioxide is increased. The pH may be more basic if the level of oxygen is increasing. The bioparameters may be computed for a single digital color image of the tissue surface or for a series of such digital color images over time.

A relative increase in the color pink over time may indicate an increase in oxygen level.

The relative levels of oxygen and carbon dioxide may have implications for the physiological status of the subject. Normally, under normal light conditions such as daylight or ambient light such as white fluorescent room light, human blood has more red than blue, more red than green and usually, although not necessarily, more green than blue. If the level of green is approaching that of red it may indicate a liver problem. When surface tissue color tends toward gray it may indicate certain heart problems. Peripheral blood (far from the heart, such as in the lips or fingers) that is blue may indicate low perfusion in the peripheral tissue.

For each surface tissue bioparameter under consideration there is a color map e.g. look up table that correlate between the color and bio parameter bio marker. The color map is a function of the following independent parameters time (temporal parameter), location (spatial parameter) and at least three basic colors. Additional depended are temporary histograms of each color, ratios such as blue/red, blue/green, green/red and certain normalization factors such Euclidian norm.

In some preferred embodiments, additional information may be used assist to in determining the value of a surface tissue bioparameter. Under some conditions the following information may be available regarding the subject from sources other than the array of photodetectors or camera: a smell emanating from the subject, the subject's sweat, heat (body temperature), tissue conductivity and tissue saltiness.

The amount of surface tissue moisture may be determined by UV light source 30. Accordingly, if the user's camera is also sensitive to UV light source, such a photodetector may capture the amount of surface tissue moisture. The computer processor producing a measurement value for surface tissue moisture by computing a quantity of white spots in the digital color image. The white spot may be invisible to the human eye.

If, on the other hand, a UV light source was not the type of light source 30 used to generate digital color image 22 and only regular white light sources or ambient light sources were used to create the digital color image, the following two-step method may be used by the system of the present invention to determine the amount of surface tissue moisture of the face of the subject from digital color image 22. First, compute the level of surface tissue smoothness. This can be achieved using local high pass filter (not shown) and neural network procedure (not shown) known in the art. Second, compute the level of surface tissue shininess. This can be accomplished by analyzing the color distribution of the high pass color image resulting from the first step and by analyzing the color distribution of the original image using a look-up table ("LUT") map and triple color histograms to determine the shininess level of the surface tissue.

In general, one or more of the following three ratios, (R-G)/(G-B) or (R-G)/(R-B) or (G-B)/(R-G), may provide additional information on the shininess of the surface tissue of the subject.

A look-up table (LUT) or a look up map (LUM) may be used to further identify certain bioparamers based on data from previously studied levels of one or more of the parameters under consideration.

Regarding the surface tissue bioparameter of surface tissue redness, when surface tissue red color is high (i.e. the red/blue ratio is high), that may indicate the presence of certain blood pressure issues or over-consumption of alcohol or a high level of surface tissue sun sensitivity. Surface tissue redness may be measured by estimating the magnitude of the difference between the levels of red, green and blue colors or by estimating the magnitude of the ratios such as blue/red, blue/green, green/red.

Surface tissue pigmentation may be measured by using UV light sources. UV images may provide information on pigments located the lower layers of the surface tissue, which are not visible to the naked eye. In the event that a UV light source is not available, the processing unit may calculate the number of local pigment spots in the surface tissue. Local pigments spots are ascertained by analyzing what is a pigment spot (spots that are not identical in color to the surrounding surface tissue area and have certain closed shape such as round shape). It is known in the art to use algorithms such neural networks, high pass filter, histograms, discontinuity in colors, topology analysis, etc. in order to identify local pigment spots.

Sun sensitivity may be ascertained by analyzing the number of pigments on the surface tissue and the surface tissue color i.e. how dark, whiteness, redness, yellowness etc. A surface tissue color LUT map may be used to configure a sun sensitivity percentage from 0 to 100 where 100 is the most sensitive.

Collagen may be ascertained by computing the level of surface tissue smoothness (well known in the literature). This may be accomplished by utilizing local high pass filter or adaptive high pass filter or topological methods, neural network methods or spectral analysis methods. The level of surface tissue smoothness is a good indicator for the level of beneath the surface tissue collagen concentration. We may set the smoothness level from 0 to 100% where 100% means very smooth surface tissue like "baby face" and thus the level of collagen is relative high. In this case the level of collagen will be at the maximum level. Conversely, aged surface tissue will have relatively low smoothness level due to wrinkles, surface tissue damage, pigments, and surface tissue dryness, all of which may suggest that the surface tissue is aged and thus has relatively low collagen concentration.

Surface tissue saturation may be indicative of the level of surface tissue vividness such as the case of snow white surface tissue or of dog fur. This parameter may be ascertained by analyzing the ratios and distance between the colors. A LUT may be used to identify surface tissue satuariton quality by using pre-study of surface tissue saturation and other bioparameters.

Hair quality is indicated by the following analysis. Hair shine may be called the saturation level of the hair. Hair shine, hair vividness and saturation may be computed from the color ratios and the magnitude of the difference between levels of the red, green and blue colors and by analyzing the Fourier spectrum of these colors. The digital color image may also reveal from the ends of the hair that the hair is broken. This may be computed by using an adaptive high pass filter. One may take digital color images of hair that is known to be have excellent quality, for example based on the appearance of the hair and based on the youth and health of the subject. Using the methods described above for skin, the colors of this reference hair is measured and recorded in a look up table (LUT) and used as a reference point. Then one may measure the hair of the subject from digital color images (using the method and apparatus as described above regarding skin) and one may then compare the color ratios and the magnitudes of the differences in colors between those of the subject and those of the reference hair, for example in the look up table, which may represent various aspects of hair quality (e.g. shininess, vividness, whether hair is broken, smoothness, etc.). A weight function of the LUT outputs may then indicate the overall hair quality. From the hair quality a treatment regimen may be siggested as per the method and apparatus of the present invention.

Surface tissue vitality (skin vitality or hair vitality) may be ascertained by arriving at a weighted function taking all the other surface tissue bioparameters into consideration and by arriving at a single scalar number from 0 to 100 where 100 is excellent vitality such as surface tissue that is as vital as baby surface tissue.

Once the surface tissue type has been ascertained, an output module 90 (which may be a cosmetic treatment output module 90 or nutrition output module 90) may output to the user a cosmetic regimen by using the table to match an identified surface tissue type with one or more cosmetic products such that each cosmetic product of the one or more cosmetic products improves at least one surface tissue surface tissue parameter of the human subject without worsening any other surface tissue parameter of the at least two (and preferably at least three) surface tissue parameters of the human subject. The cosmetic regimen may be outputted to the user at the same web site 20 which the user transmitted the digital color image 22, to another web site (not shown) or to another location in cyberspace or otherwise. In some preferred embodiments, the cosmetic treatment output module 90 may output the cosmetic regimen within thirty seconds of the user transmitting the digital color image (or in the case of the we cam, within thirty seconds of the taking of the image), or in some preferred embodiments, within 15 or 45 or 60 or 90 or 120 seconds.

Nutrition output module 90 may output a nutrition regimen in which each food improves at least one surface tissue parameter of the human subject without worsening any other surface tissue parameter of the at least two surface tissue parameters of the human subject In order to accelerate the outputting of the cosmetic or nutrition regimen to the user in as short a time period as possible, for example, less than 30 seconds, less than 20 seconds or less than 15 seconds, the user device may incorporate the program code 61. Alternatively, select portions of the program code 61 may be so incorporated into the user device. This may be accomplished by obtaining permission from the user and then installing program code 61 or selected portions thereof into the user's cellular telephone or other user device. The selected portions can for example be those elements of program code 61 described in discussing FIG. 1 and FIG. 2 above, Regarding the collection of value ranges for different surface tissue parameters, in some embodiments the value range can be a single scalar number rather than a true range of numbers. Each element in the collection may express a value range for a different surface tissue parameter.

A first color, a second color and a third color shall be understood to refer the colors that together determine a color spectrum. One example of such a set of three colors that determine a color spectrum is red, green, and blue (in any order). Another example of such a color combination is yellow, cyan and magenta, brown (in any order), The difference between sets may be due to the choice of white versus black background.

The present invention may also be described as a method 100 of providing a cosmetic and nutrition regimen for a human from digital color video image of a face of the human sent to a web site. Method 100 may include a step 110 of using at least one color image sensor to detect red light, blue light and green light reflected from a digital color image, and to produce a series of spatial temporal electric signals from the detected red, blue and green lights. A further step 120 may comprise having a computer processor verify that the digital color image is of live human tissue by at least two of (i) comparing levels of red, blue and green to boundary-reference levels, (ii) comparing levels of red, blue and green to each other and determining which level of at least one of red, green and blue is greater than another at least one of red, green and blue, (iii) comparing to a reference ratio or to a reference ratio range at least one of a ratio of blue/red, a ratio of blue/green and a ratio of green/red, and (iv) measuring over time increases or decreases in at least one of a ratio of blue/red, a ratio of blue/green, a ratio of green/red, a level of red, a level of blue and a level of green.

In a further step 130 of method 100, if the photo is determined to be human tissue, a computer processor may generates a color intensity distribution over time from the series of spatial temporal electric signals. This may be a level over time of each of the three colors. In step 140, the computer processor, for each of at least two surface tissue parameters relating to a surface tissue of the face and including at least one of (in other preferred embodiments at least two of or at least three of or all four parameters) surface tissue pH, surface tissue moisture, surface tissue collagen level and surface tissue sun sensitivity, may produce a measurement value of the each surface tissue parameter of the at least two surface tissue parameters by analyzing the color intensity distribution of the first, second and third color in space (for example three dimensional space) over time and identifying at least one of a correlation and a look-up table between a level of the each surface tissue parameter and at least one of color distribution and any changes in color distribution in a color intensity distribution over time of any of the first color, the second color, and the third color. A step 150 may involve the processor converting each measurement value into a value range, each surface tissue parameter having at least three value ranges.

Method 100 may also include a step 160 of a computer processor identifying a surface tissue type associated with the digital color image from a multiplicity of surface tissue types using each value range of each of the at least two (and preferably is at least three) surface tissue parameters. Each surface tissue type may represent a collection of value ranges for different particular surface tissue parameters, the number of surface tissue types equalling $X^Y$, wherein X is a number of value ranges and Y is a number of different surface tissue parameters, wherein X is at least three and wherein Y is at least two. Preferably Y is at least three. In some preferred embodiments, Y is 4 or 5 or 6 or 7 or 8. The computer processor may produce measurement values for each of at least three of surface tissue pH, surface tissue moisture, surface tissue collagen level and surface tissue sun sensitivity, or in some preferred embodiments, for each of surface tissue pH, surface tissue moisture, surface tissue collagen level and surface tissue sun sensitivity.

In some preferred embodiments, method 100 includes a step of the computer processor producing a measurement value for surface tissue moisture by computing a quantity of white spots in the digital color image. In this case, a UV light source was used to produce the digital image 22. In some other preferred embodiments, method 100 includes a step of the computer processor producing a measurement value for surface tissue sun sensitivity by computing a quantity of dark spots in the digital color image. In this case also, the light source 30 was a UV light source. In some embodiments of method 100, there is also a step of providing to users a UV light source and a user creating the digital color image using the UV light source.

Method 100 may also include a step 170 of an output module outputting to the user a cosmetic regimen and/or a nutrition regimen by matching an identified surface tissue type with one or more cosmetic products (or with one or more nutrition products), such that each cosmetic product of the one or more cosmetic products improves at least one surface tissue surface tissue parameter of the human subject without worsening any other surface tissue parameter of the at least two (and preferably at least three) surface tissue parameters of the human subject.

In some preferred embodiments, method 100 may include a step of collecting and analyzing feedback from the user concerning a surface tissue parameter after the human subject uses the cosmetic regimen. The method may also include a step of, after the cosmetic regimen was outputted to the user, receiving at least one further digital color video image of the surface tissue from the user; and a step of tracking changes in the at least two surface tissue parameters (in other preferred embodiments in at least three or at least four surface tissue parameters) for the surface tissue by comparing the further digital color video image with previously provided digital color video images and adjusting the cosmetic regimen based on the tracked changes.

In some preferred embodiments of the present invention, the owner of the system of the present invention may prearrange with reputable cosmetic companies, for example those that may have a wide range of cosmetic proiducts for the surface tissue or otherwise, that the system owner will include in the cosmetic regimen outputted to users a recommendation for the particular products of the cosmetic manufacturer in exchange for a percentage of the revenues from the sale of the product. This provides an incentive for the cosmetic manufacturers to discuss the ingredients of the cosmetic products with the system owner so as to match cosmetic products with surface tissue types such that at least one surface tissue parameter is improved without hurting a different surface tissue parameter. For example, a skin tissue may have a pH of 4.8 and normal moisture level. The treatment for improving the skin pH from 4.8 to 5.5 should not hurt the normal level of the skin moisture. For example, after treatment the skin moisture should not become too dry or too oily.

While the invention has been described with respect to a limited number of embodiments, it will be appreciated that many variations, modifications and other applications of the invention may be made. Therefore, the claimed invention as recited in the claims that follow is not limited to the embodiments described herein.

What is claimed is:

1. A system that uses at least one color digital image for providing a cosmetic regimen to a user at a web site, comprising:
   a computer server associated with the web site, at least one of the computer server and the web site configured to prompt the user to transmit at least one digital color image of a surface tissue of a human subject to the computer server,
   a computer memory storing (i) the at least one digital color image, (ii) a multiplicity of surface tissue types, (iii) at least one of a list of cosmetic products and a list of nutrition products, and (iv) a table matching each surface tissue type to a product from the list;
   a local high pass filter;
   one or more processors configured to execute program code;
   the program code configured to create a color intensity distribution from the at least one digital color image and, for each of at least three surface tissue parameter relating to the surface tissue, configured to produce a measurement value of each surface tissue parameter by analyzing the color intensity distribution and at least one of identifying a correlation between and using a look-up table comparing, a level of each surface tissue parameter and at least one of (i) color distribution and (ii) changes, if any, in color distribution, wherein the at least three surface tissue parameters include surface tissue moisture, surface tissue pH and at least one of (i) surface tissue collagen level, (ii) redness and/or pigmentation and (iii) surface tissue sun sensitivity,
   wherein the program code is configured to produce the measurement value of the surface tissue moisture, by determining a level of surface tissue smoothness and a level of surface tissue shininess if the light source is of ambient light or white light, and by determining a quantity of white spots in the at least one digital color image if the light source is a UV light source, wherein the level of surface tissue smoothness is determined using the local high pass filter;

the program code configured to convert each measurement value into a value range, each surface tissue parameter having at least three value ranges;

the program code configured to determine that the at least one digital color image is of live human tissue and neither of dead tissue nor of an inanimate object, by at least two of (i) comparing levels of red to boundary-reference levels of red, comparing levels of blue to boundary-reference levels of blue and comparing levels of green to boundary-reference levels of green, (ii) comparing levels of red to levels of blue and to levels of green, comparing levels of blue to levels of red and to levels of green and comparing levels of green to levels of blue and to levels of red and determining which level of at least one of red, green and blue is equal or greater than another at least one of red, green and blue, (iii) comparing to a reference ratio or to a reference ratio range at least one of a ratio of blue/red, a ratio of blue/green and a ratio of green/red, and (iv) measuring over time increases or decreases in at least one of a ratio of blue/red, a ratio of blue/green, a ratio of green/red, a level of red, a level of blue and a level of green;

the program code configured, in response to the user's transmission of the at least one digital color image, to generate a surface tissue type associated with the at least one digital color image, the surface tissue type synthesized from measurement values or value ranges of the at least three surface tissue parameters, each of the at least three surface tissue parameters having at least three possible measurement values, said surface tissue type different from any surface tissue parameter;

the program code configured, using each value range of each of the surface tissue parameters, to identify a surface tissue type associated with the at least one digital color image from the multiplicity of surface tissue types; and a cosmetic treatment output module configured to output to the user, within 60 seconds of the user transmitting the at least one digital color image, a cosmetic regimen by using the table to match an identified surface tissue type with one or more cosmetic products such that each cosmetic product improves at least one surface tissue parameter of the human subject so as to become closer to a normal level without worsening any other surface tissue parameter of the at least three surface tissue parameters of the human subject so as to be further from the normal level, wherein at least one of the following is true: (i) improving the skin pH to become closer to the normal skin pH level does not move a level of the skin moisture away from a normal skin moisture level and (ii) improving a level of the skin moisture to become closer to normal does not move a level of the skin pH away from a normal skin pH, each surface tissue type representing a collection of value ranges for different particular surface tissue parameters of the at least three surface tissue parameters, the number of surface tissue types equaling $X^Y$, wherein X is a number of value ranges and Y is a number of different surface tissue parameters, wherein X is at least three and wherein Y is at least 3.

2. The system of claim 1, wherein each ingredient of a cosmetic product of the one or more cosmetic products improves at least one surface tissue parameter of the human subject so as to become closer to a normal level without worsening any other surface tissue parameter of the at least three surface tissue parameters of the human subject so as to be further from the normal level.

3. The system of claim 1, wherein Y is at least 4.

4. The system of claim 1, wherein the surface tissue parameters include surface tissue pH, surface tissue collagen level and surface tissue sun sensitivity.

5. The system of claim 1, wherein the surface tissue parameters include at least two of (i) surface tissue collagen level, (ii) redness and/or pigmentation and (iii) surface tissue sun sensitivity.

6. The system of claim 1, wherein the surface tissue parameters include at least three of (i) surface tissue collagen level, (ii) at least one of redness and pigmentation, (iii) surface tissue sun sensitivity, (iv) tissue $SpO_2$, (v) $CO_2$, (vi) wrinkles, (vii) acne, (viii) sweat and (ix) tissue smoothness.

7. The system of claim 1, wherein the at least one digital color image includes at least two different digital color images.

8. The system of claim 1, wherein the at least one digital color image is at least two digital color images, the system further comprising a web cam that captures and transmits the at least two digital color images in real time from the user to the web site.

9. The system of claim 1, wherein the at least one digital color image is at least two digital color images, the system further comprising the cosmetic regimen output module outputting the cosmetic regimen within 30 seconds of the user transmitting the at least two digital color images.

10. The system of claim 1, wherein the at least one digital color image is at least two digital color images, the system further comprising
the computer memory also storing a list of foods and a table matching each surface tissue type to a food in the list of foods; and
wherein the program code is further configured to output a nutrition regimen in which each food improves at least one surface tissue parameter of the human subject so as to become closer to a normal level without worsening any other surface tissue parameter of the at least three surface tissue parameters of the human subject so as to be further from the normal level,
wherein the program code is further configured, after generating the surface tissue type associated with the images, to prompt the user to select at least one of a cosmetic regimen and a nutrition regimen.

11. The system of claim 1, further comprising cosmetic products, each cosmetic product identifying thereon each surface tissue type for which each cosmetic product improves at least one surface tissue parameter so as to become closer to the normal level without worsening any other surface tissue parameter of the at least three surface tissue parameters so as to be further from the normal level.

12. The system of claim 1, wherein the level of surface tissue shininess is also determined by one or more of the following three ratios: (i) (the level of red minus the level of green/(the level of green minus the level of blue), (ii) (the level of red minus the level of green)/(the level of red minus the level of blue), (iii) (the level of green minus the level of blue)/(the level of red minus the level of green).

13. The system of claim 1, wherein the at least three surface tissue parameters include skin vitality, and wherein skin vitality is a numerical ranking representing a weighted function of all other surface tissue parameters.

14. The system of claim 1, wherein the one or more processors are configured by program code to measure over time increases or decreases in at least one of the ratio of blue/red, the ratio of blue/green, the ratio of green/red, the level of red, the level of blue and the level of green.

15. The system of claim 1, wherein the one or more processors are configured by the program code to determine that the digital color image is of live human tissue and neither of dead tissue nor of an inanimate object, by (i) comparing levels of red to boundary-reference levels of red, comparing levels of blue to boundary-reference levels of blue and comparing levels of green to boundary-reference levels of green, (ii) comparing levels of red to levels of blue and to levels of green, comparing levels of blue to levels of red and to levels of green and comparing levels of green to levels of blue and to levels of red and determining which level of at least one of red, green and blue is equal or greater than another at least one of red, green and blue, (iii) comparing to a reference ratio or to a reference ratio range at least one of a ratio of blue/red, a ratio of blue/green and a ratio of green/red, and (iv) measuring over time increases or decreases in at least one of a ratio of blue/red, a ratio of blue/green, a ratio of green/red, a level of red, a level of blue and a level of green.

16. The system of claim 1, wherein the surface tissue encompasses both skin and hair such that the system is configured to output the cosmetic regimen within the 60 seconds of the user transmitting to the web site the digital color image of the skin and is configured to output the cosmetic regimen within the 60 seconds of the user transmitting to the web site the digital color image of the hair.

17. A method of using at least one digital color image and a processor to provide a human user at a web site with a cosmetic and nutrition regimen suitable for the human user, comprising:
   prompting the human user, using a computer server associated with the web site, to transmit at least one digital color image of a surface tissue of a human subject to the computer server;
   determining, using one or more computer processors configured by program code, that the at least one digital color image is of live human tissue and is neither of dead tissue nor of an inanimate object by at least two of (i) comparing levels of red to boundary-reference levels of red, comparing levels of blue to boundary-reference levels of blue and comparing levels of green to boundary-reference levels of green, (ii) comparing levels of red to levels of blue and to levels of green, comparing levels of blue to levels of red and to levels of green and comparing levels of green to levels of blue and to levels of red and determining which level of at least one of red, green and blue is equal or greater than another at least one of red, green and blue, (iii) comparing to a reference ratio or to a reference ratio range at least one of a ratio of blue/red, a ratio of blue/green and a ratio of green/red, and (iv) measuring over time increases or decreases in at least one of a ratio of blue/red, a ratio of blue/green, a ratio of green/red, a level of red, a level of blue and a level of green;
   if the at least one digital color image is determined to be live human tissue, generating, by the one or more computer processors, a color intensity distribution from the at least one digital color image;
   producing, by the one or more computer processors, for each of the surface tissue parameters, including surface tissue moisture, and surface tissue pH and at least one of (i) surface tissue collagen level, (ii) redness and/or pigmentation and (iii) surface tissue sun sensitivity, a measurement value of each surface tissue parameter by analyzing the color intensity distribution and at least one of identifying a correlation between, and using a look-up table comparing, a level of each surface tissue parameter and at least one of color distribution and any changes in the color intensity distribution,
   wherein the one or more processors produce the measurement value of the surface tissue moisture, by determining a level of surface tissue smoothness and a level of surface tissue shininess if the light source is of ambient light or white light, and by determining a quantity of white spots in the digital color image if the light source is a UV light source, wherein the level of surface tissue smoothness is determined using a local high pass filter;
   converting, using the one or more processors, each measurement value into a value range, each surface tissue parameter having at least three value ranges;
   automatically in response to the human user's transmission of the at least one digital color image, generating, by the one or more computer processors, a surface tissue type associated with the at least one digital color image, the surface tissue type synthesized from measurement values or value ranges of at least three surface tissue parameters, each of the at least three surface tissue parameters having at least three possible measurement values, said surface tissue type different from any surface tissue parameter;
   outputting to the human user, by a cosmetic treatment output module, within 60 seconds of the human user's transmission of the at least one digital color image to the computer server, a cosmetic regimen by matching the generated surface tissue type with one or more cosmetic products, such that each cosmetic product of the one or more cosmetic products improves at least one surface tissue parameter of the human subject so as to become closer to a normal level without worsening any other surface tissue parameter of the at least three surface tissue parameters so as to be further from the normal level, wherein at least one of the following is true: (i) improving the skin pH to become closer to the normal skin pH level does not move a level of the skin moisture away from a normal skin moisture level and (ii) improving a level of the skin moisture to become closer to normal does not move a level of the skin pH away from a normal skin pH.

18. The method of claim 17, further comprising each surface tissue type representing a collection of value ranges for different particular surface tissue parameters, the number of surface tissue types equaling $X^Y$, wherein X is a number of value ranges and Y is a number of different surface tissue parameters, wherein X is at least three and wherein Y is at least 4.

19. The method of claim 17, further comprising the one or more processors generating the surface tissue type associated with the at least one digital color image such that the surface tissue type is synthesized from measurement values or value ranges of each of surface tissue pH, surface tissue moisture, surface tissue collagen level and of at least one of redness, pigmentation and surface tissue sun sensitivity, tissue $SpO_2$, $CO_2$, wrinkles, acne, sweat and tissue smoothness.

20. The method of claim 19, further comprising the one or more processors producing a measurement value for surface tissue sun sensitivity by computing a quantity of dark spots in the at least one digital color image.

21. The method of claim 17, further comprising the one or more processors producing measurement values for each of surface tissue pH, surface tissue moisture, surface tissue collagen level and surface tissue sun sensitivity.

22. The method of claim 17, further comprising providing to human users a UV light source and the human user creating the at least one digital color image using the UV light source.

23. The method of claim 17, wherein the surface tissue encompasses both skin and hair such that the method is configured to output the cosmetic regimen within the 60 seconds of the human user transmitting to the web site the at least one digital color image of the skin and is configured to output the cosmetic regimen within the 60 seconds of the human user transmitting to the web site the at least one digital color image of the hair.

24. The method of claim 17, further comprising collecting feedback from the human user either concerning a surface tissue parameter or an additional digital color image, analyzing, by the one or more processors, the feedback from the human user after the human subject uses the cosmetic regimen and generating a new regimen based on the collected feedback.

25. The method of claim 17, further comprising after the cosmetic regimen was outputted to the human user, receiving at least one further digital color image of the surface tissue from the human user;
   tracking quantitative changes in the at least three surface tissue parameters for the surface tissue by comparing the at least one further digital color image with previously provided at least one digital color image and outputting an adjusted cosmetic regimen based on the tracked quantitative changes; and
   the output module also outputting a graphical depiction of the quantitative changes in the at least three surface tissue parameters.

26. The method of claim 17, further comprising if the at least one digital color image is determined to not likely be that of live human tissue, outputting a notice to the user that either advises the human user concerning changing the light used to generate the at least one digital color image or advises the human user concerning checking the light used to generate the at least one digital color image.

27. The method of claim 17, further comprising if the at least one digital color image is determined to not likely be that of live human tissue, the cosmetic treatment output module outputting a notice concerning utilizing daylight or white ambient light in generating the at least one digital color image.

28. The method of claim 17, further comprising if the at least one digital color image is determined to not likely be that of live human tissue, outputting a notice concerning utilizing daylight or white ambient light as close to daylight as possible in generating the digital color image.

29. The method of claim 17, wherein the at least three surface tissue parameters include skin vitality, and wherein skin vitality is a numerical ranking representing a weighted function of all other surface tissue parameters.

30. A non-transitory computer-readable medium having stored thereon program code, the program code executed by one or more processors, the execution of the program code by the one or more processors performing:
   prompting a user to transmit at least one digital color image of a surface tissue of a human subject to a computer server associated with a web site;
   storing on a memory storage device (i) the at least one digital color image, (ii) a multiplicity of surface tissue types, (iii) a list of cosmetic products, and (iv) a table matching each surface tissue type to a product from the list,
   creating a color intensity distribution from the at least one digital color image and, for each of at least three surface tissue parameters relating to the surface tissue, configured to produce a measurement value of each surface tissue parameter by analyzing the color intensity distribution and at least one of identifying a correlation between and using a look-up table comparing, a level of each surface tissue parameter and at least one of (i) color distribution and (ii) changes, if any, in color distribution, wherein the at least three surface tissue parameters include surface tissue moisture, surface tissue pH and at least one of (i) surface tissue collagen level, (ii) redness and/or pigmentation and (iii) surface tissue sun sensitivity,
   wherein the program code is configured to produce the measurement value of the surface tissue moisture, by determining a level of surface tissue smoothness and a level of surface tissue shininess if the light source is of ambient light or white light, and by determining a quantity of white spots in the digital color image if the light source is a UV light source;
   converting each measurement value into a value range, each surface tissue parameter having at least three value ranges;
   determining that the at least one digital color image is of live human tissue, by at least one of (i) comparing levels of red to boundary-reference levels of red, comparing levels of blue to boundary-reference levels of blue and comparing levels of green to boundary-reference levels of green, (ii) comparing levels of red to levels of blue and to levels of green, comparing levels of blue to levels of red and to levels of green and comparing levels of green to levels of blue and to levels of red and determining which level of at least one of red, green and blue is equal or greater than another at least one of red, green and blue, (iii) comparing to a reference ratio or to a reference ratio range at least one of a ratio of blue/red, a ratio of blue/green and a ratio of green/red, and (iv) measuring over time increases or decreases in at least one of a ratio of blue/red, a ratio of blue/green, a ratio of green/red, a level of red, a level of blue and a level of green;
   in response to the user's transmission of the digital color image, generating a surface tissue type associated with the at least one digital color image, the surface tissue type synthesized from measurement values or value ranges of the at least three surface tissue parameters, each of the at least three surface tissue parameters having at least three possible measurement values, said surface tissue type different from any surface tissue parameter;
   using each value range of each of the surface tissue parameters, identifying a surface tissue type associated with the at least one digital color image from the multiplicity of surface tissue types; and
   using a cosmetic treatment output module, outputting to the user, within 60 seconds of the user transmitting the at least one digital color image, a cosmetic regimen by using the table to match an identified surface tissue type with one or more cosmetic products such that each cosmetic product improves at least one surface tissue surface tissue parameter of the human subject so as to become closer to a normal level without worsening any other surface tissue parameter of the at least three surface tissue parameters of the human subject so as to be further from the normal level, wherein at least one of the following is true: (i) improving the skin pH to become closer to the normal skin pH level does not move a level of the skin moisture away from a normal skin moisture level and (ii) improving a level of the skin moisture to become closer to normal does not move a level of the skin pH away from a normal skin pH, each surface tissue type representing a collection of value ranges for different particular surface tissue parameters of the at least three surface tissue parameters, the number of surface tissue types equaling $X^Y$, wherein X is a number of value ranges and Y is a number of different surface tissue parameters, wherein X is at least three and wherein Y is at least 3.

\* \* \* \* \*